US010068330B2

(12) United States Patent
Parthasarathy et al.

(10) Patent No.: US 10,068,330 B2
(45) Date of Patent: Sep. 4, 2018

(54) AUTOMATIC SEGMENTATION OF BREAST TISSUE IN A THERMOGRAPHIC IMAGE

(71) Applicant: Niramai Health Analytix Pvt Ltd, Bangalore (IN)

(72) Inventors: Arun Koushik Parthasarathy, Karnataka (IN); Krithika Venkataramani, Bangalore (IN); Siva Teja Kakileti, Andhra Pradesh (IN)

(*) Notice: Subject to any disclaimer, the term of this patent is extended or adjusted under 35 U.S.C. 154(b) by 149 days.

(21) Appl. No.: 15/055,140

(22) Filed: Feb. 26, 2016

(65) Prior Publication Data

US 2017/0249734 A1  Aug. 31, 2017

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0091* (2013.01); *A61B 5/015* (2013.01); *A61B 5/4312* (2013.01); *A61B 10/0041* (2013.01); *G06K 9/00201* (2013.01); *G06K 9/00624* (2013.01); *G06K 9/4604* (2013.01); *G06K 9/4652* (2013.01); *G06K 9/52* (2013.01); *G06T 7/0085* (2013.01); *G06T 7/408* (2013.01); (Continued)

(58) Field of Classification Search
CPC ... A61B 5/0091; A61B 5/015; A61B 10/0041; G06K 9/4604; G06K 9/4652; G06K 9/52; G06T 7/0085; G06T 7/408; G06T 7/60; G06T 7/0012; G06T 2207/10048; G06T 2207/30068
See application file for complete search history.

(56) References Cited

U.S. PATENT DOCUMENTS 5,859,891 A    1/1999 Hibbard
6,511,426 B1*  1/2003 Hossack .............. G01S 15/899
                                              600/437
(Continued)

OTHER PUBLICATIONS

EtehadTavakol, M., et al. "Estimating the mutual information between bilateral breast in thermograms using nonparametric windows." Journal of medical systems 35.5 (2011): 959-967.*

(Continued)

*Primary Examiner* — Shefali Goradia
(74) *Attorney, Agent, or Firm* — The Law Office of Austin Bonderer, PC; Austin Bonderer

(57) ABSTRACT

What is disclosed is a system and method for automatically segmenting a breast from surrounding tissue in a thermal image. A thermal image of at least one breast of the patient is received. The thermal image is then analyzed to identify a set of N points around the breast, a contour of an outline of the body, and isotherms of the axilla and infra-mammary fold. Thereafter, the points are connected together to form a N-sided irregular polygon which segments the breast from surrounding tissue. Each of the points is a vertex of the polygon and comprises a draggable object which enables a user to selectively manipulate a shape of the polygon. A user can add/delete vertices from the polygon as desired. The area of the image encompassed by the polygon is communicated to a breast cancer screening algorithm performing automated or semi-automated screening.

12 Claims, 9 Drawing Sheets

(51) Int. Cl.
- A61B 5/00 (2006.01)
- A61B 5/01 (2006.01)
- A61B 10/00 (2006.01)
- G06K 9/46 (2006.01)
- G06K 9/52 (2006.01)
- G06T 7/40 (2017.01)
- G06T 7/60 (2017.01)
- G06T 7/90 (2017.01)

(52) U.S. Cl.
CPC .......... *G06T 7/60* (2013.01); *G06T 7/90* (2017.01); *A61B 2576/02* (2013.01); *G06K 2209/05* (2013.01); *G06T 2207/10048* (2013.01); *G06T 2207/30068* (2013.01)

(56) References Cited

U.S. PATENT DOCUMENTS

| | | | | |
|---|---|---|---|---|
| 8,923,954 | B2* | 12/2014 | Herman | A61B 5/0064 382/128 |
| 9,256,799 | B2* | 2/2016 | Wehnes | A61B 6/5211 |
| 9,292,755 | B2 | 3/2016 | Aller et al. | |
| 9,486,146 | B2* | 11/2016 | Venkataramani | G06T 7/136 |
| 2007/0276228 | A1* | 11/2007 | Vining | A61B 5/1076 600/425 |
| 2008/0159613 | A1* | 7/2008 | Luo | G06T 7/0012 382/132 |
| 2009/0310835 | A1* | 12/2009 | Kaus | G06T 17/20 382/128 |
| 2016/0027182 | A1* | 1/2016 | Oh | G06T 7/0051 382/131 |

OTHER PUBLICATIONS

Borchartt, T., et al., "Breast thermography from an image processing viewpoint: A survey," in Signal Processing, vol. 93, 2013, pp. 2785-2803.
Scales, N., et al., "Automated image segmentation for breast analysis using infrared images," Engineering in Medicine and Biology Society, 2004. IEMBS'04. 26th Annual International Conference of the IEEE (vol. 1, pp. 1737-1740).
Luis-Garcia, R., et al. "A fully automatic algorithm for contour detection of bones in hand radiographs using active contours," IImage Processing, 2003. ICIP 2003. Proceedings. 2003 International Conference (vol. 3, pp. III-421).
Manoj, R., et al., "A Survey of Segmentation in Mass Detection Algorithm for Mammography and Thermography," International Journal of Advanced Electrical and Electronics Engineering, 2012, pp. 70-77, vol. 1, Issue 2.
About Meditherm, Digital Infrared Thermal Imaging, 2 pp. downloaded from the Internet Jan. 2, 2016.
Benoso, B., et al., "An Automated Method for Segmentation of the Breast in Mammography Images," Int. J. Contemp. Math. Sciences, 2013, vol. 8, Issue 15, pp. 731-742.
Qi, L., et al., "Asymmetry Analysis Using Automatic Segmentation and Classification for Breast Cancer Detection in Thermograms," Engineering in Medicine and Biology Society, 2001. Proceedings of the 23rd Annual International Conference of the IEEE (vol. 3, pp. 2866-2869).
Motta, L., et al. Automatic segmentation on thermograms in order to aid diagnosis and 2D modeling. In Proceedings of 10th Workshop em Informática Médica (vol. 1, pp. 1610-1619).
Qi, et al., "Detecting breast cancer from infrared images by asymmetry analysis." Engineering in Medicine and Biology Society, 2000. Proceedings of the 22nd Annual International Conference of the IEEE. vol. 2. IEEE, 2000.
Jadin, M. S., et al., M. A. B. (Mar. 2011). "Image processing methods for evaluating infrared thermographic image of electrical equipments. In Progress in electromagnetics research symposium proceedings," Marrakesh, Morocco, pp. 1299-1302.
Selvarasu, N., et al., (2012). "Image processing techniques and neural networks for automated cancer analysis from breast thermographs—a review." Indian Journal of Computer Science and Engineering (IJCSE), 3(1), pp. 133-137.
Kapoor, P., & Patni, S. (2012). "Image segmentation and asymmetry analysis of breast thermograms for tumor detection," International Journal of Computer Applications, vol. 50, Issue 9.
NoTouch Software Analytics, 2 pages, downloaded from the Internet Jan. 2, 2016.
Ng, E. Y. K., et al. (2006). "Segmentation of breast thermogram: improved boundary detection with modified snake algorithm," Journal of Mechanics in Medicine and Biology, 6(02), 123-136.
Yasmin, M., et al. (2013). "Survey paper on diagnosis of breast cancer using image processing techniques," Research Journal of Recent Sciences ISSN, pp. 2277, 2502.
Sawyer, R., CS 299 Project Milestone Report: Automated Segmentation of Breast Density, PSU.Edu.
Literature Review of Breast Thermography.

\* cited by examiner

US 10,068,330 B2

AUTOMATIC SEGMENTATION OF BREAST TISSUE IN A THERMOGRAPHIC IMAGE

TECHNICAL FIELD

The present invention is directed to systems and methods for automatically segmenting breast tissue from surrounding tissue in a thermal image of a patient for breast cancer screening.

BACKGROUND

Automated thermographic screening can be very useful and effective for conducting breast cancer screening where knowledge and expertise of the specific Region of Interest (ROI) of the breast is required to separate a specific region of interest from surrounding tissues which are of no interest so that the identified tissue can be further analyzed and subsequently classified as being cancerous or non-cancerous. Extraction of one or more regions of interest in a thermo graphic image of is a challenging task due to the amorphous nature of the tissue undergoing examination. Although experts can segment the breast tissue into regions of interest by visual inspection after years of experience, it becomes a difficult task to manage effectively when the number of patients being screened is larger than a few. As sophisticated software tools for breast cancer screening arise in the medical software arts, there is an increasing need for methods which can automatically identify and segment regions of interest in a thermographic image of a patient's breast. The teachings hereof are specifically directed to this ongoing effort.

Accordingly, what is needed in this art are increasingly sophisticated systems and methods for automatically segmenting breast tissue from surrounding tissue in a thermal image of a patient for breast cancer screening.

BRIEF SUMMARY

What is disclosed is a system and method for automatically segmenting breast tissue from surrounding tissue in a thermal image of a patient for breast cancer screening. One embodiment of the present method involves the following. First, a thermographic image of at least one breast of a person undergoing breast cancer screening is received. Pixels in the thermographic image with a higher temperature value are displayed in a first color and pixels with a lower temperature value are displayed in a second color. Pixels with temperature values between the lower and higher temperature values are displayed in gradations of color between the first and second colors. The thermographic image is then analyzed to identify a set of N≥5 points around the breast based on a contour of an outline of the body and the isotherms of the axilla and infra-mammary fold. Thereafter, the points are connected, in a piecewise linear fashion, to form a N-sided polygon which segments the breast from surrounding tissue. Each of the points is a vertex of the polygon and comprises a draggable object which enables a user to selectively manipulate a shape of the polygon. The teachings hereof find their uses in a breast cancer screening software tool.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which:

FIG. 5 shows a thermal image of an oblique (angle) view of the left breast of a woman wherein N=9 points have been identified to define a 9-sided polygon which segments the breast from surrounding tissue in the thermal image;

DETAILED DESCRIPTION

What is disclosed is a system and method for automatically segmenting breast tissue from surrounding tissue in a thermal image of a patient for breast cancer screening. The teachings hereof find their intended uses in a software interface tool performing automated or semi-automated breast cancer screening.

A "person" refers to either a male or a female. Gender pronouns are not to be viewed as limiting the scope of the appended claims strictly to females. Moreover, although the term "person" or "patient" is used interchangeably throughout this disclosure, it should be appreciated that the person undergoing breast cancer screening may be something other than a human such as, for example, a primate. Therefore, the use of such terms is not to be viewed as limiting the scope of the appended claims to humans.

Figure 1:
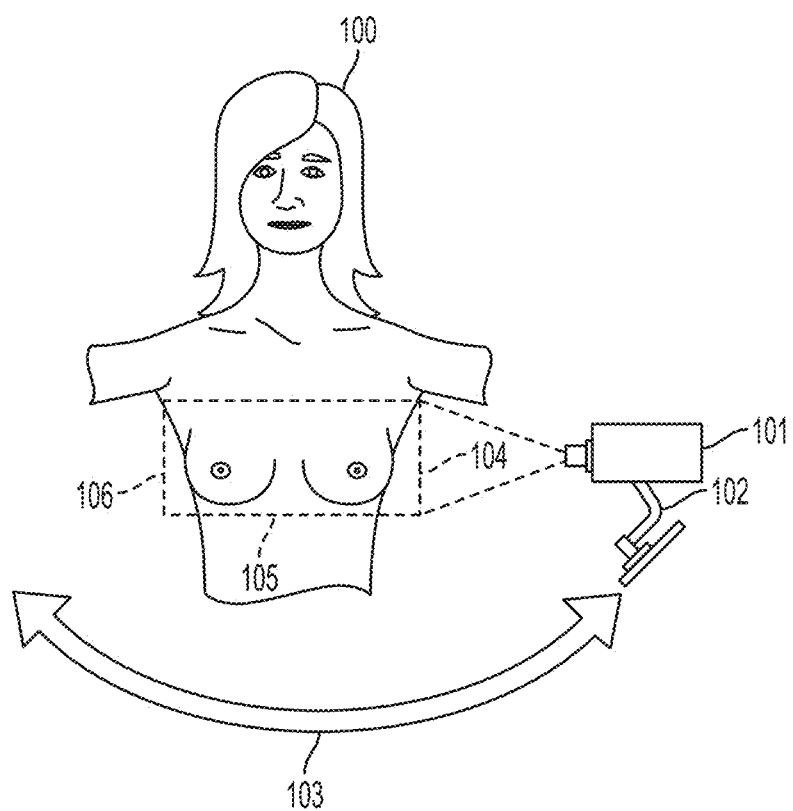
FIG. 1 shows an example female patient with a thermal camera mounted on a slideable and axially rotatable robotic arm for moving the camera along a semi-circular trajectory from side-to-side in front of the patient.

A "breast area" refers to tissue of the breast and may further include surrounding tissue as is deemed appropriate for breast cancer screening. Thermal images are capture of the breast area in various view angles which include a mediolateral view (center chest), a mediolateral oblique (angular) view, and a lateral (side) view, as are generally understood in the medical imaging arts. It should be appreciated that the mediolateral view is a supplementary mammographic view which generally shows less breast tissue and pectoral muscle than the mediolateral oblique view. FIG. 1 shows the breast area of a female 100. It should be appreciated that the patient can be stationary while the camera moves about the patient, or the patient can move while the camera remains stationary, or the patient and the camera can move to capture the appropriate view angles as desired.

A "thermal camera" refers to either a still camera or a video camera with a lens that focuses infrared energy from objects in a scene onto an array of specialized sensors which convert infrared energy across a desired thermal wavelength band into electrical signals on a per-pixel basis and which output an array of pixels with colors that correspond to temperatures of the objects in the image. FIG. 1 shows a thermal camera 101 mounted on a slideable and axially rotatable robotic arm 102 capable of moving the camera along a semi-circular trajectory 103 in the front of the patient from side-to-side such that thermographic images can be captured in a right-side view 104, a front view 105, and a left-side view 106, and various oblique angles in between. The thermal camera can be a single-band infrared camera, a multi-band infrared camera in the thermal range, and a hyperspectral infrared camera in the thermal range. The resolution of a thermal camera is effectively the size of the pixel. Smaller pixels mean that the resulting image with have a higher resolution and thus better spatial definition. Although thermal cameras offer a relatively large dynamic range of temperature settings, it is preferable that the camera's temperature range be relatively small, centered around the person's body surface temperature so that small temperature variations are amplified in terms of pixel color changes in order to provide a better measure of temperature variation. Thermal cameras are readily available in various streams of commerce.

Figure 2:
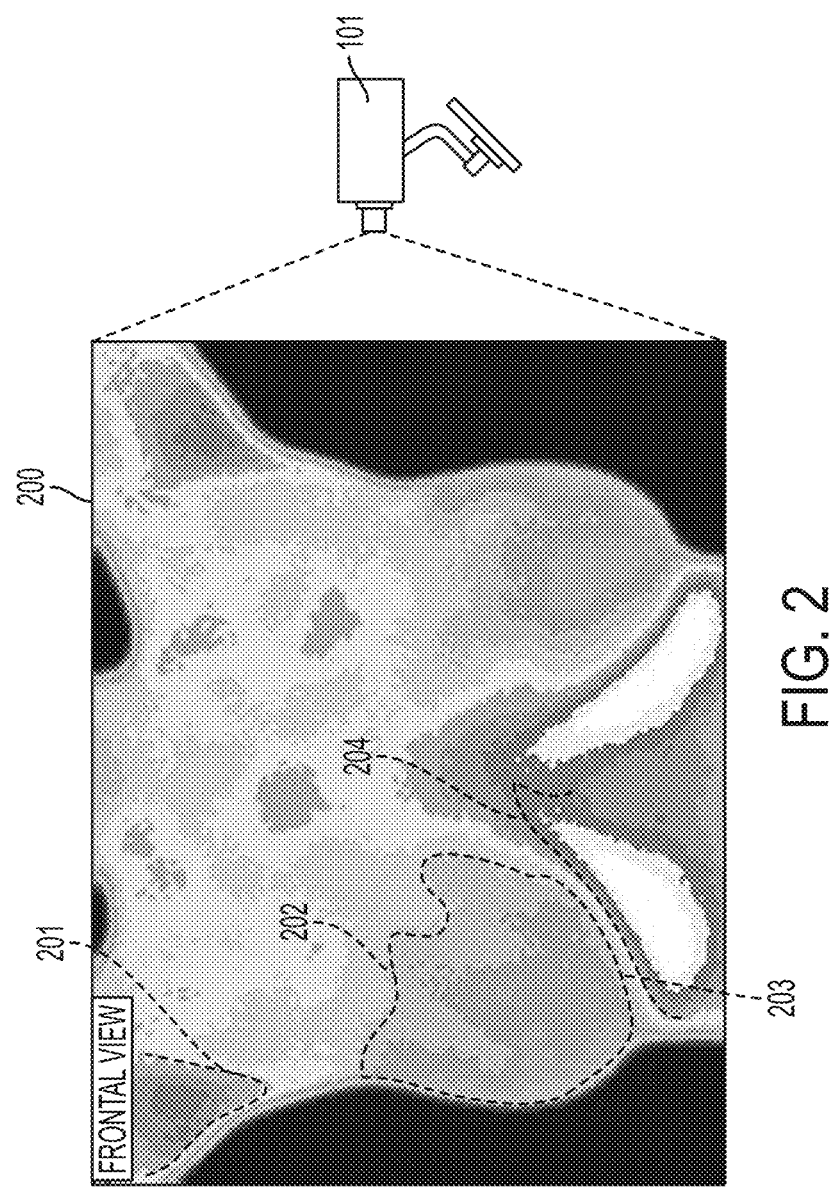
FIG. 2 shows a thermal image of the breast area of a woman wherein boundary lines of various isotherms have been identified.

A "thermographic image" or simply a "thermal image" is an image captured by a thermal camera. The thermographic image comprises an array of color pixels with each color being associated with a temperature. Pixels with a higher temperature value are displayed in the thermal image in a first color and pixels with a lower temperature value are displayed in a second color. Pixels with temperature values between the lower and higher temperature values are displayed in gradations of color between the first and second colors. FIG. 2 shows a thermal image 200 of a center front view of a breast area. Although shown in black/white, it should be appreciated that the thermal image is a color image. Dashed line 201 shows a lower boundary of the isotherm of the axilla. Dashed line 202 show an upper boundary of the isotherm of the breast. Dashed line 203 shows a lower boundary of the isotherm of the breast. Dashed line 204 shows an upper boundary of the isotherm of the inframammary fold. Thermal images are communicated to a workstation which runs a computer program for which analyzes the thermographic image(s) in accordance with the teachings hereof.

"Receiving a thermal image" of a patient for cancer screening is intended to be widely construed and includes retrieving, capturing, acquiring, or otherwise obtaining video image frames. The image can be received or retrieved from a remote device over a network, or from a media such as a CDROM or DVD. The image may be downloaded from a web-based system or application which makes video available for processing in accordance with the methods disclosed herein. The image can also be received from an application such as those which are available for handheld cellular devices and processed on the cellphone or other handheld computing device such as an iPad or Tablet-PC. The image can be received directly from a memory or storage device of the imaging device used to capture that image or video. The received thermal image is analyzed.

"Analyzing the thermographic image" means to identify a plurality of points $P_N$ in the image, where $N \geq 3$. In one embodiment, $N \geq 10$. The points are based on each of: a lower boundary of the isotherm of the patient's axilla, an upper boundary of the isotherm of the patient's infra-mammary fold, and a contour of an outline of the patient's body.

Figure 3:
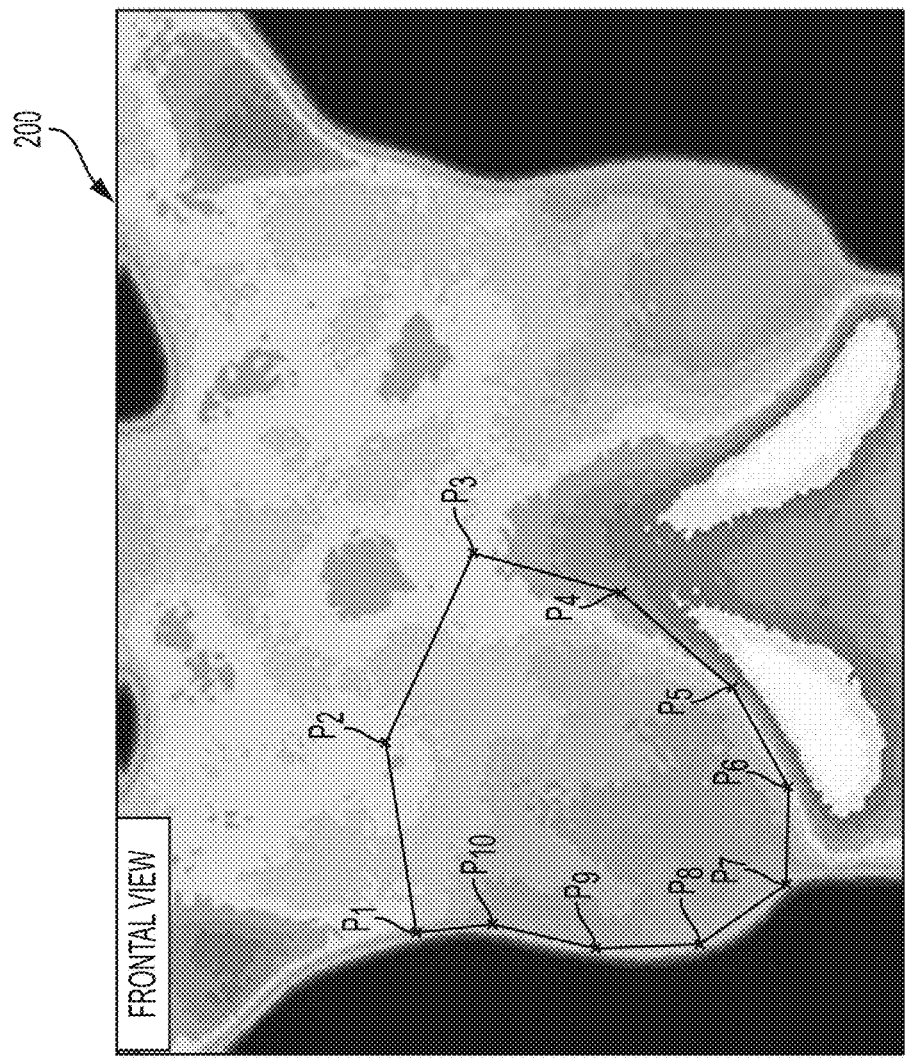
FIG. 3 shows a thermal image of FIG. 2 wherein N=10 points have been identified based on the boundary lines of the isotherms in FIG. 2.

Reference is now being made to FIG. 3 which shows N=10 points identified in the thermal image of FIG. 2. Starting at point $P_1$ and proceeding clockwise, $P_1$ lies along a contour edge of the body. Points $P_2$, $P_3$ lie between a lower boundary of the axilla 201 and an upper boundary of the isotherm 202 of the breast. Points $P_4$, $P_5$, $P_6$, $P_7$ lie between a lower boundary of the isotherm 203 of the breast and an upper boundary of the isotherm 204 of the infra-mammary fold. Points $P_8$, $P_9$, $P_{10}$ lay along a contour of edge of the body. As shown, the points are vertices which, when connected together, define a boundary of a 10-sided irregular polygon which segments the breast from surrounding tissue in the thermal image. A similar process would be used for other breast in the image.

Figure 4:
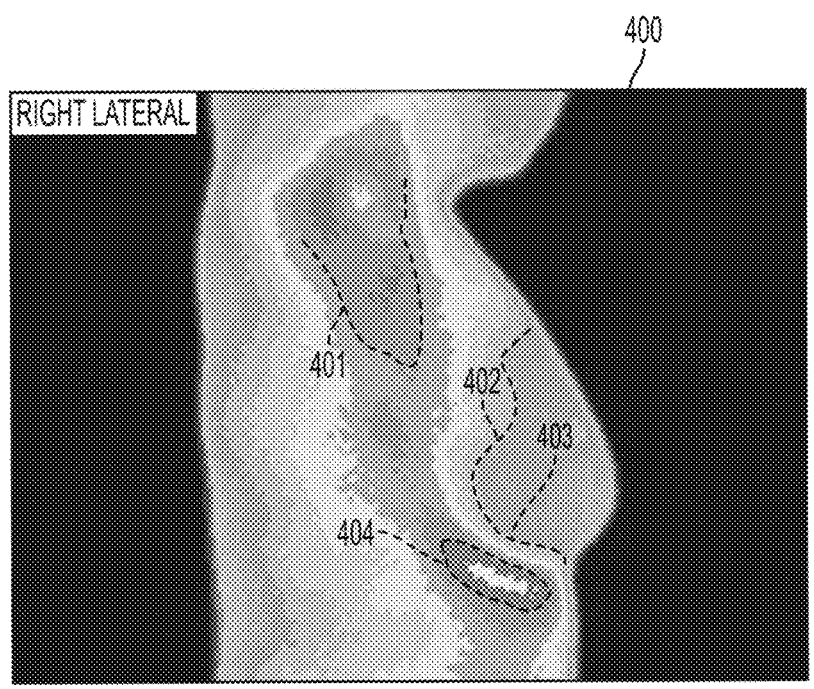
FIG. 4 is a thermal image of a side view of a breast area wherein boundary lines of various isotherms have been identified.

Reference is now being made to FIG. 4 which shows a thermal image 400 of a side view of a breast. Dashed line 401 shows a lower boundary of the isotherm of the axilla. Dashed line 402 shows an upper boundary of the isotherm of the breast. Dashed line 403 shows a lower boundary of the isotherm of the breast. Dashed line 404 shows an upper boundary of the isotherm of the infra-mammary fold.

Figure 5:
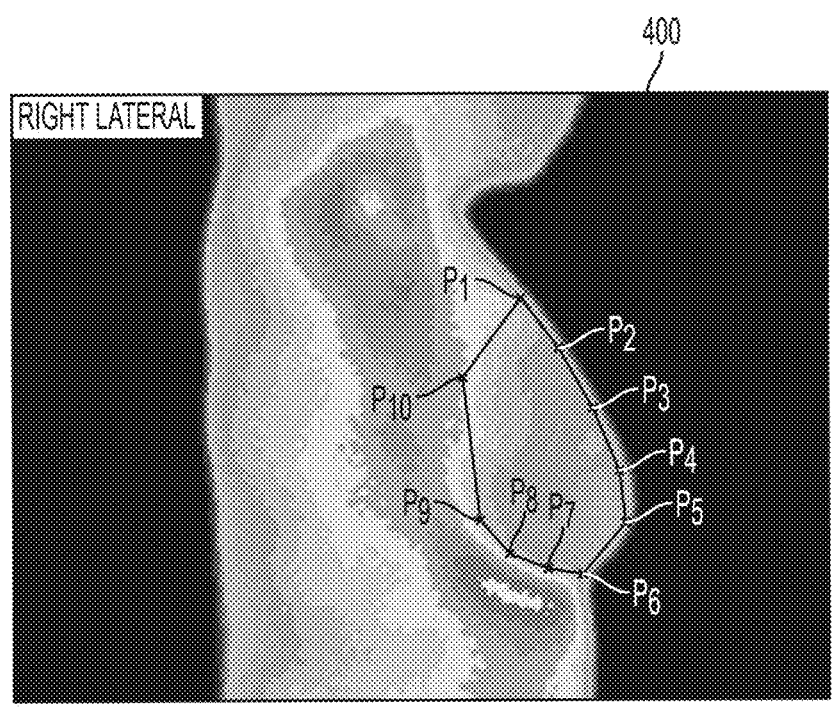
FIG. 5 shows a thermal image of FIG. 4 wherein N=10 points have been identified based on the boundary lines of the isotherms in FIG. 4.

Reference is now being made to FIG. 5 which shows N=10 points identified in the thermal image of FIG. 4. Starting at point $P_1$ and proceeding clockwise, points $P_1$, $P_2$, $P_3$, $P_4$, $P_5$, $P_6$ lie along a contour edge of the body. Points $P_7$, $P_8$, $P_9$ lie between a lower boundary of the isotherm 403 of the breast and an upper boundary of the isotherm 404 of the infra-mammary fold and. Points $P_{10}$ lie between a lower boundary of the isotherm 401 of the axilla and an upper boundary of the isotherm 402 of the breast. As shown, the points are vertices which, when connected together, define a boundary of a 10-sided irregular polygon which segments the breast from surrounding tissue in the thermal image. A similar process would be used for other breast in the image.

Figure 6:
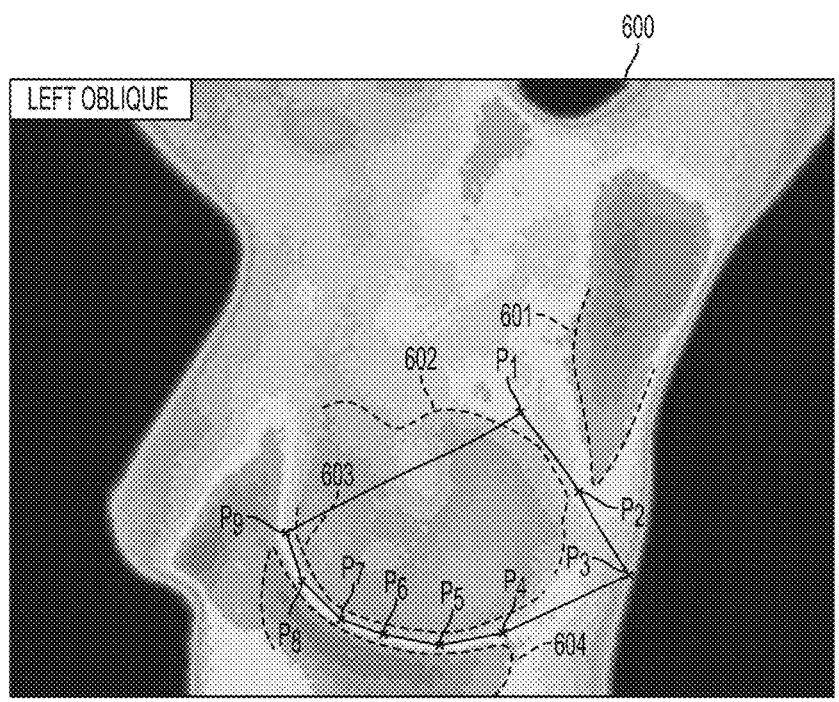
FIG. 6 shows the polygon of FIG. 5 wherein the user has added new vertices $P_{10}$ and $P_{11}$ and has shifted the location of point $P_{13}$ such that the polygon encompasses only breast tissue of interest.

Reference is now being made to FIG. 6 which shows a thermal image 600 of an oblique view of the breast area of a woman. A lower boundary of the isotherm of the axilla is shown at 601. An upper boundary of the isotherm of the breast is shown at 602. A lower boundary of the isotherm of the breast is shown at 603. An upper boundary of the isotherm of the infra-mammary fold is shown at 604. Starting at point $P_1$ and proceeding clockwise, points $P_1$ and $P_2$ lie between a lower boundary of the isotherm 601 of the axilla and an upper boundary of the isotherm 602 of the breast. Point $P_3$ resides along a contour edge of the body. Points $P_3$ through $P_9$ lie between a lower boundary of the isotherm 602 of the breast and an upper boundary of the isotherm 604 of the infra-mammary fold. As shown in FIG. 6, the N=9 points are connected to define a boundary of a 9-sided irregular polygon. What is also disclosed is an embodiment wherein each of the vertices of the polygon displayed on the display device for the user comprise draggable objects which enable the user to selectively manipulate the shape of the polygon. The user is further enabled to add one or more new vertices to the polygon and remove vertices from the polygon as needed prior.

Figure 7:
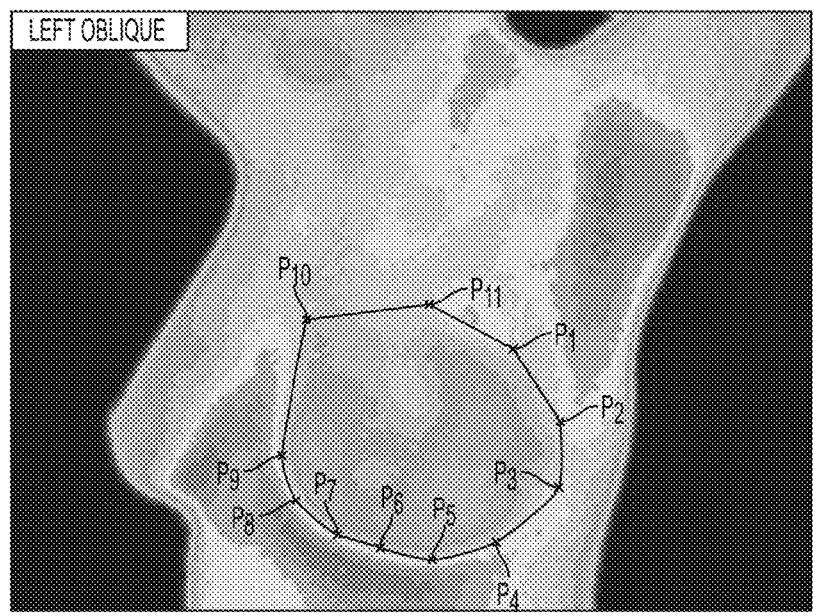
FIG. 7 shows the user having selectively added new vertices $P_{10}$ and $P_{11}$ to the polygon of FIG. 6, such that a boundary of the polygon encompasses additional tissue of interest.

Reference is now being made to FIG. 7 which shows the user having selectively added vertices $P_{10}$ and $P_{11}$ to the polygon of FIG. 6, such that the polygon further encompasses additional tissue of interest. Further, the user has also shifted the location of point $P_3$ from along the contour of the body's edge to a position that is closer to the breast tissue. Once the user is satisfied with the polygon, the area encompassed by the polygon is communicated to a software interface tool performing tumor detection and/or a tumor classification.

A "software interface tool" is a composite of functionality for tumor detection and/or tumor classification using a plurality of user-selectable objects displayed on a display device such as a touchscreen display. One embodiment of a software interface tool which implements a tumor detection method is disclosed in commonly owned and co-pending U.S. patent application Ser. No. 14/668,178, entitled: "Software Interface Tool For Breast Cancer Screening", by Krithika Venkataramani et al. Another embodiment of a software interface tool which implements a tumor classification method is disclosed in commonly owned and co-pending U.S. patent application Ser. No. 15/053,767, entitled: "Software Interface Tool For Breast Cancer Screening", by Gayatri Sivakumar et al. Various embodiments of the software interface tool perform manual, semi-automatic, and automatic selection of a block of pixels in the thermal image for screening.

It should be appreciated that the steps of "receiving", "analyzing", "communicating", "performing", "determining", "connecting", "identifying" and the like, as used herein, include the application of any of a variety of techniques as well as mathematical operations according to any specific context or for any specific purpose. It should be appreciated that such steps may be facilitated or otherwise effectuated by a microprocessor executing machine readable program instructions such that an intended functionality can be effectively performed.

Example Flow Diagram

Figure 8:
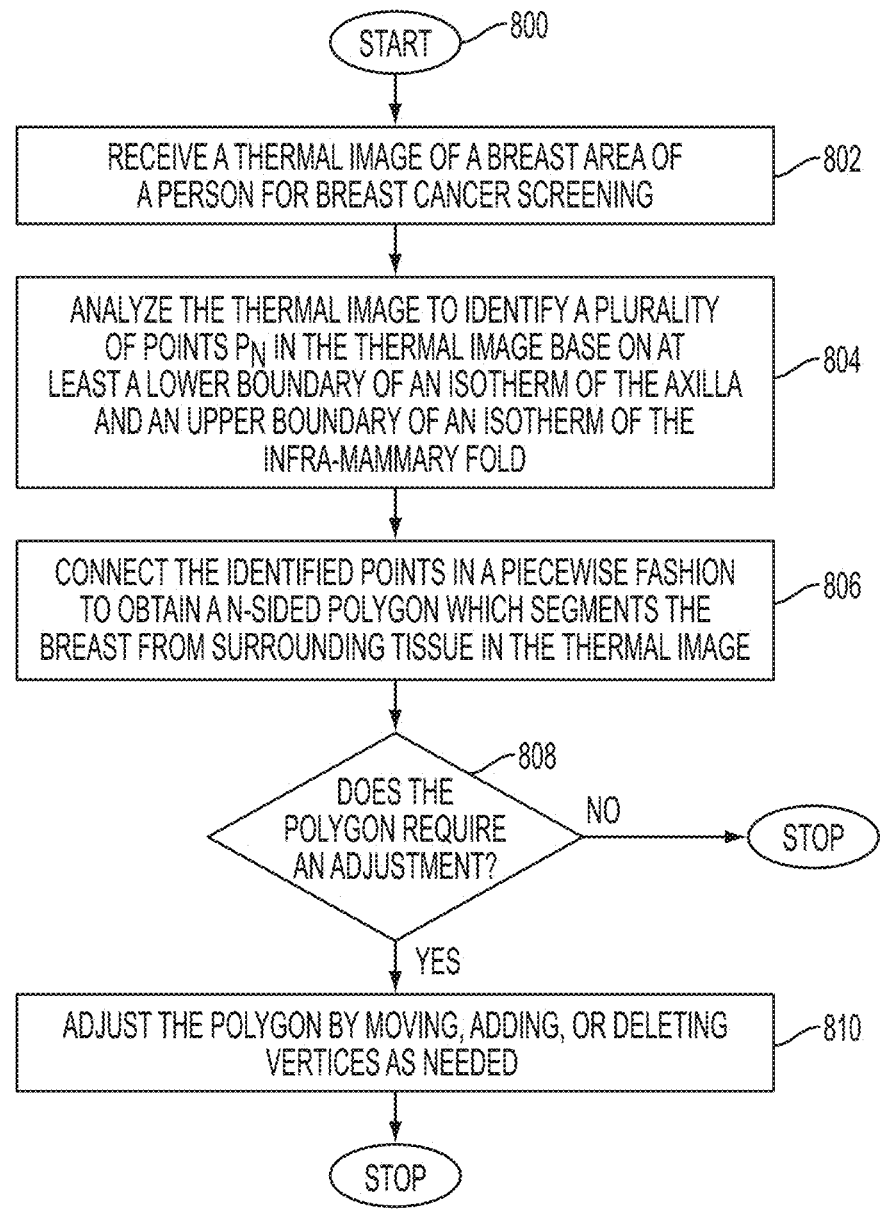
FIG. 8 is a flow diagram of one embodiment of the present method for segmenting a breast from surrounding tissue in a thermographic image for breast cancer screening.

Reference is now being made to the flow diagram of FIG. 8 which shows one example embodiment of the present method for segmenting a breast from surrounding tissue in a thermographic image for breast cancer screening. Flow processing begins at step 800 and immediately proceeds to step 802.

At step 802, receive a thermal image of a breast area of a person for breast cancer screening. The term "receiving" is intended to be widely construed and includes: retrieving, capturing, acquiring, or otherwise obtaining a thermal image for automatic breast segmentation in accordance with the teachings hereof. The thermal images can be retrieved from a memory or storage device of the thermal camera or retrieved from a media such as a CDROM or DVD. Thermal images can be obtained from a remote device over a network or downloaded from a web-based system or application which makes thermal images available for processing. The thermal images may be pre-processed as needed. FIG. 1 shows an example of a thermal camera capturing a thermal image of a female patient. Various aspects of the methods disclosed herein may be performed by a processor inside the thermal camera which executes machine readable program instructions for automatic breast segmentation.

At step 804, analyze the thermal image to identify a plurality of points $P_N$ based on at least a lower boundary of the isotherm of the axilla and an upper boundary of the isotherm of the infra-mammary fold. In other embodiments, an outline contour of the body's edge is further used to identify the points.

At step 806, connect the identified points in a piecewise fashion to obtain a N-sided polygon which segments the breast from surrounding tissue in the thermal image. Various aspects of analyzing the thermal image to obtain points and to form a polygon from those vertices are shown and discussed with respect to the embodiments of FIGS. 3-7.

At step 808, a determination is made whether the polygon requires adjustment. If so then, at step 810, adjust the polygon by moving, adding, or deleting vertices as desired.

At step 812, communicate an area encompassed by the polygon to a breast cancer screening algorithm. Thereafter, in this embodiment, further processing stops.

It should be appreciated that the flow diagrams hereof are illustrative. One or more operative steps may be added, modified or enhanced. Such variations are intended to fall within the scope of the appended claims. All or portions of the flow diagrams may be implemented partially or fully in hardware in conjunction with machine executable program instructions.

Example Image Processing System

Figure 9:
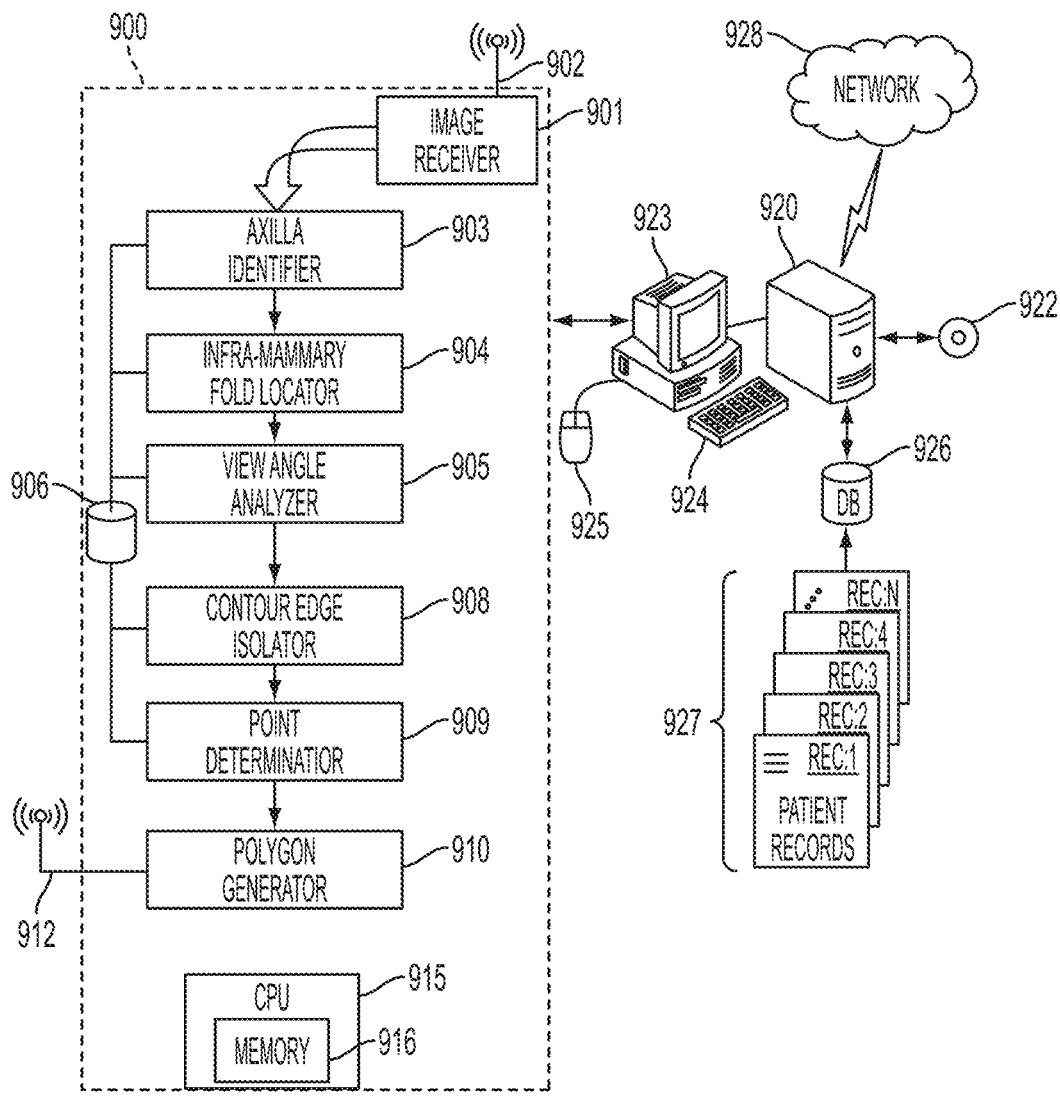
FIG. 9 is a block diagram of one example image processing system 900 for processing a thermal image in accordance with the embodiments described with respect to the flow diagram of FIG. 8.

Reference is now being made to FIG. 9 which shows a block diagram of one example image processing system 900 for processing a thermal image in accordance with the embodiments described with respect to the flow diagram of FIG. 8.

Image Receiver 901 wirelessly receives the captured thermal images via antenna 902 having been transmitted thereto from the thermal camera 101 of FIG. 1. Axial Identifier Module 903 analyzes the received thermal image to identify a lower boundary of an isotherm of one or both of the patient's right and left axilla. A result thereof is stored to storage device 906. Infra-Mammary Fold Locator Module analyzes the thermal image to identify an upper boundary of the isotherm of one or both of the patient's infra-mammary folds. A result thereof is stored to storage device 906. View Angle Analyzer 905 determines the view angle of the received thermal image which, in turn, is stored to storage device 906. Contour Edge Isolator 908 analyzes the thermal image to find a contour edge around the breast area with respect to a background and stores the result to storage device 906. Once the image has been analyzed, Point Determinator Module 908 retrieves the various results from storage device 906 and proceeds to identify N points. Such points are shown and discussed with respect to FIGS. 3-7. Polygon Generator 910 receives the points from Module 908 and proceeds to connect the identified points to together to form a N-sided polygon. The polygon is wirelessly communicated via antenna 912 to the workstation 920 wherein the polygon is overlaid onto the thermal image for viewing by the user using the display device 923. Various thresholds and user-defined parameters which may be used to identify the points and connect the points to form a polygon can be retrieved from storage device 906 using a communication pathway (not shown).

Central Processing Unit 915 retrieves machine readable program instructions from a memory 916 and is provided to facilitate the functionality of any of the modules of the system 900. CPU 915, operating alone or in conjunction with other processors, may be configured to assist or otherwise perform the functionality of any of the modules or processing units of the image processing system 900 as well as facilitating communication between the system 900 and the workstation 920.

Workstation 920 has a computer case which houses various components such as a motherboard with a processor and memory, a network card, a video card, a hard drive capable of reading/writing to machine readable media 922 such as a floppy disk, optical disk, CD-ROM, DVD, magnetic tape, and the like, and other software and hardware as is needed to perform the functionality of a computer workstation. The workstation includes a display device 923, such as a CRT, LCD, or touchscreen display, for displaying information, regions of interest, thermal images, lines, points, distances, features, view angles, computed values, thresholds, medical information, patient data, results, and the like, some or all of which may be produced or otherwise generated by any of the modules or processing units of the image processing system 900. A user can view any information and make a selection from various menu options displayed thereon. Keyboard 924 and mouse 925 effectuate a user input or selection. The user input may take the form of a user moving, adding, or deleting vertices of the polygon shown on the thermal image.

It should be appreciated that the workstation 920 has an operating system and other specialized software configured to display alphanumeric values, menus, scroll bars, dials, slideable bars, pull-down options, selectable buttons, and the like, for entering, selecting, modifying, and accepting information needed for performing various aspects of the methods disclosed herein. A user may use the workstation to identify a set of images of interest, set various parameters, and otherwise facilitate the functionality of any of the modules or processing units of the video processing system. A user or technician may utilize the workstation to modify, add or delete any of the features disclosed herein, as is deemed appropriate. A user or technician may adjust various parameters being utilized or dynamically adjust in real-time various system or threshold settings or any parameters of the thermal camera used to capture the thermal images. User inputs and selections may be stored/retrieved in any of the storage devices 906, 922 and 926. Default settings and initial parameters can be retrieved from any of the storage devices.

Although shown as a desktop computer, it should be appreciated that the workstation can be a laptop, mainframe, tablet, notebook, smartphone, or a special purpose computer such as an ASIC, or the like. The embodiment of the workstation is illustrative and may include other functionality known in the arts.

The workstation implements a database in storage device 926 wherein records are stored, manipulated, and retrieved in response to a query. Such records, in various embodiments, take the form of patient medical histories stored in association with information identifying the patient (collectively at 927). It should be appreciated that the database may be the same as storage device 906 or, if separate devices, may contain some or all of the information contained in any of the storage devices shown. Although the database is shown as an external device, the database may be internal to the workstation mounted, for example, on a hard drive within the computer case.

Any of the components of the workstation may be placed in communication with any of the modules of the image processing system 900 or any devices placed in communication therewith. Moreover, any of the modules of the image processing system 900 can be placed in communication with storage device 926 and/or computer readable media 922 and may store/retrieve therefrom data, variables, records, parameters, functions, and/or machine readable/executable program instructions, as needed to perform their intended functionality. Any of the modules or processing units of the image processing system 900 may be placed in communication with one or more remote devices over network 928.

It should be appreciated that some or all of the functionality performed by any of the modules or processing units of the image processing system 900 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

The teachings hereof can be implemented in hardware or software using any known or later developed systems, structures, devices, and/or software by those skilled in the applicable arts without undue experimentation from the functional description provided herein with a general knowledge of the relevant arts. Software applications may be executed by processors on different hardware platforms or emulated in a virtual environment and may leverage off-the-shelf software. One or more aspects of the methods described herein are intended to be incorporated in an article of manufacture. The article of manufacture may be shipped, sold, leased, or otherwise provided separately either alone or as part of a product suite or a service. The above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any publications referenced herein are incorporated in their entirety by reference having been made thereto.

What is claimed is:

1. A method for segmenting a breast from surrounding tissue in a thermographic image for breast cancer screening, the method comprising:

receiving a thermal image of an upper body of a person, which represents temperature distribution on a breast area of the person as pixels in the thermal image with a highest temperature value being displayed in a first color and pixels with a lowest temperature value being displayed in a second color, pixels with temperature values between the lowest and highest temperature values being displayed in gradations of color between the first and second colors, wherein the thermal image is captured by a thermal imaging camera, the thermal imaging camera comprising:
 an array of sensors that converts infrared energy into electrical signals on a per-pixel basis;
 a lens that focuses the infrared energy from the person's breast onto the array of sensors, wherein the array of sensors detects temperature values from the person's breast; and
 a specialized processor that processes the detected temperature values into at least one block of pixels to generate the thermal image;

analyzing, using an image processing technique, the thermal image to identify a plurality of points $P_N$, where $N \geq 5$, in the thermal image surrounding the breast area, wherein the analyzing of the thermal image comprises determining a view angle of the thermal image,
 determining a contour of an outline of an edge of the breast area of the person;
 determining an upper boundary and a lower boundary of an isotherm of the breast;
 determining a lower boundary of an isotherm of axilla of the person; and
 determining an upper boundary of an isotherm of infra-mammary fold of the person;

generating a N-sided polygon by connecting the points together to segment the breast from surrounding tissue in the thermal image; and transforming the thermal image into a segmented thermal image by overlaying the N-sided polygon onto the thermal image, wherein the segmented thermal image is configured for analysis using a breast cancer screening algorithm for screening the breast cancer.

2. The method of claim 1, wherein identifying points comprises:
identifying points which lie along the contour of the outline of the edge of the breast area of the person;
identifying points which lie between the lower boundary of the isotherm of the axilla and the upper boundary of the isotherm of the breast; and
identifying points which lie between the lower boundary of the isotherm of the breast and the upper boundary of the isotherm of the inframammary fold.

3. The method of claim 1, wherein each of vertices of the polygon comprise draggable objects, further comprising a user to selectively manipulating a shape of the polygon.

4. The method of claim 1, further comprising communicating at least a portion of an area of the segmented thermal image encompassed by the polygon to the breast cancer screening algorithm.

5. The method of claim 1, further comprising one of: a user adding at least one new vertex into the polygon, and a user deleting at least one vertex from the polygon.

6. The method of claim 1, wherein when said N-sided polygon is a 10-sided irregular polygon, the identifying points comprises
identifying points $P_1$, $P_7$, $P_8$, $P_9$ and $P_{10}$ which lie along the contour of the outline of the edge of the breast area of the person;
identifying points $P_1$, $P_2$ and $P_3$ which lie between the lower boundary of the isotherm of the axilla and the upper boundary of the isotherm of the breast; and
identifying points $P_4$, $P_5$, $P_6$ and $P_7$ which lie between the lower boundary of the isotherm of the breast and the upper boundary of the isotherm of the inframammary fold.

7. The method of claim 1, wherein when said N-sided polygon is a 9-sided irregular polygon, the identifying points comprises
identifying points $P_1$ and $P_2$ which lie between the lower boundary of the isotherm of the axilla and the upper boundary of the isotherm of the breast;
identifying point $P_3$ which resides along a contour of the outline of the edge of the breast area of the person; and
identifying points $P_3$ through $P_9$ which lie between the lower boundary of the isotherm of the breast and the upper boundary of the isotherm of the inframammary fold.

8. The method of claim 7, wherein the method comprises shifting a location of the point $P_3$ from along the contour edge of the breast to a position that is closer to the breast tissue.

9. A system for segmenting a breast from surrounding tissue in a thermographic image for breast cancer screening, the system comprising:
a storage device;
a processor in communication with the storage device, the processor executing machine readable instructions for performing:
receiving a thermal image of an upper body of a person, which represents temperature distribution on a breast area of the person as pixels in the thermal image with a highest temperature value being displayed in a first color and pixels with a lowest temperature value being displayed in a second color, pixels with temperature values between the lowest and highest temperature values being displayed in gradations of color between the first and second colors, wherein the thermal image is captured by a thermal imaging camera, the thermal imaging camera comprising:
an array of sensors that converts infrared energy into electrical signals on a per-pixel basis;
a lens that focuses the infrared energy from the person's breast onto the array of sensors, wherein the array of sensors detects temperature values from the person's breast; and
a specialized processor that processes the detected temperature values into at least one block of pixels to generate the thermal image;
analyzing, using an image processing technique, the thermal image to identify a plurality of points $P_N$, where N≥3, in the thermal image surrounding the breast area, wherein the analyzing of the thermal image comprises
determining a view angle of the thermal image,
determining a contour of an outline of an edge of the breast area of the person;
determining an upper boundary and a lower boundary of an isotherm of the breast;
determining a lower boundary of an isotherm of axilla of the person; and
determining an upper boundary of an isotherm of infra-mammary fold of the person;
generating N-sided polygon by connecting the points together to segment the breast from surrounding tissue in the thermal image; and
transforming the thermal image into a segmented thermal image by overlaying the N-sided polygon onto the thermal image, wherein the segmented thermal image is configured for analysis using a breast cancer screening algorithm for screening the breast cancer.

10. The system of claim 9, wherein identifying points comprises:
identifying points which lie along the contour of the outline of the edge of the breast area of the person;
identifying points which lie between the lower boundary of the isotherm of the axilla and the upper boundary of the isotherm of the breast; and
identifying points which lie between the lower boundary of the isotherm of the breast and the upper boundary of the isotherm of the inframammary fold.

11. The system of claim 9, wherein each of vertices of the polygon comprise draggable objects, further comprising a user to selectively manipulating a shape of the polygon.

12. The system of claim 9, further comprising communicating at least a portion of an area of the segmented thermal image encompassed by the polygon to the breast cancer screening algorithm.

* * * * *